(12) United States Patent
Schaub et al.

(10) Patent No.: US 11,413,610 B2
(45) Date of Patent: Aug. 16, 2022

(54) USE OF A TRANSITION METAL CATALYST COMPRISING A TETRADENTATE LIGAND FOR HYDROGENATION OF ESTERS AND/OR FORMATION OF ESTERS, A PROCESS FOR HYDROGENATION OF ESTERS, A PROCESS FOR FORMATION OF ESTERS AND A TRANSITION METAL COMPLEX COMPRISING SAID TETRADENTATE LIGAND

(71) Applicant: BASF SE, Ludwigshafen am Rhein (DE)

(72) Inventors: Thomas Schaub, Ludwigshafen (DE); Aviel Anaby, Schwaebisch Hall (DE); Mathias Schelwies, Ludwigshafen (DE); Rocco Paciello, Ludwigshafen (DE); Jonas Schwaben, Ludwigshafen (DE); A. Stephen K. Hashmi, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 17 days.

(21) Appl. No.: 16/961,053

(22) PCT Filed: Jan. 10, 2019

(86) PCT No.: PCT/EP2019/050552
§ 371 (c)(1),
(2) Date: Jul. 9, 2020

(87) PCT Pub. No.: WO2019/138000
PCT Pub. Date: Jul. 18, 2019

(65) Prior Publication Data
US 2020/0398261 A1 Dec. 24, 2020

(30) Foreign Application Priority Data
Jan. 10, 2018 (EP) .................................. 18150967

(51) Int. Cl.
*B01J 31/18* (2006.01)
*C07C 67/40* (2006.01)
*B01J 31/12* (2006.01)

(52) U.S. Cl.
CPC ............ *B01J 31/189* (2013.01); *C07C 67/40* (2013.01); *B01J 31/121* (2013.01); *B01J 2231/763* (2013.01); *B01J 2531/0258* (2013.01); *B01J 2531/821* (2013.01)

(58) Field of Classification Search
None
See application file for complete search history.

(56) References Cited

U.S. PATENT DOCUMENTS

| 8,471,048 B2 | 6/2013 | Kuriyama et al. |
| 8,524,953 B2 | 9/2013 | Kuriyama et al. |
| 2011/0237814 A1 | 9/2011 | Kuriyama et al. |
| 2015/0202609 A1 | 7/2015 | Goussev et al. |

(Continued)

FOREIGN PATENT DOCUMENTS

| EP | 1 868 964 A1 | 12/2007 |
| EP | 1 868 965 A1 | 12/2007 |

(Continued)

OTHER PUBLICATIONS

Krishnakumar et al. Inorganic Chemistry, 56, 7278-7284 (Year: 2017).*

(Continued)

*Primary Examiner* — Yun Qian
(74) *Attorney, Agent, or Firm* — Lowenstein Sandler LLP

(57) ABSTRACT

The present invention relates to the use of a transition metal catalyst TMC1, which comprises a transition metal M selected from metals of groups 7, 8, 9 and 10 of the periodic table of elements according to IUPAC and a tetradentate ligand of formula I wherein $R^1$ are identical or different and are each an organic radical having from 1 to 40 carbon atoms, and $R^2$ are identical or different and are each an organic radical having from 1 to 40 carbon atoms, as catalyst in processes for formation of compounds comprising at least one carboxylic acid ester functional group —O—C(=O)— starting from at least one primary alcohol and/or hydrogenation of compounds comprising at least one carboxylic acid ester functional group —O—C(=O)—. The present invention further relates to a process for hydrogenation of a compound comprising at least one carboxylic acid ester functional group —O—C(=O)—, to a process for the formation of a compound comprising at least one carboxylic acid ester functional group —O—C(=O)— by dehydrogenase coupling of at least one primary alcohol with a second alcoholic OH-group, to a transition metal complex comprising the tetradentate ligand of formula I and to a process for preparing said transition metal complex.

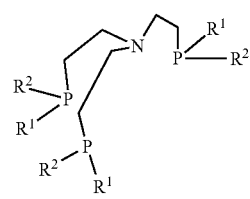

I

15 Claims, No Drawings

(56) References Cited

U.S. PATENT DOCUMENTS

| | | |
|---|---|---|
| 2016/0288111 A1 | 10/2016 | Dumeignil et al. |
| 2016/0326199 A1 | 11/2016 | Geisser et al. |
| 2017/0073298 A1 | 3/2017 | Goussev et al. |

FOREIGN PATENT DOCUMENTS

| | | |
|---|---|---|
| WO | WO 2006/106483 A1 | 10/2006 |
| WO | WO 2006/106484 A1 | 10/2006 |
| WO | WO 2012/052996 A2 | 4/2012 |
| WO | WO 2013/023307 A1 | 2/2013 |
| WO | WO 2016/035080 A1 | 3/2016 |

OTHER PUBLICATIONS

International Search Report dated May 20, 2019 in PCT/EP2019/050552, 5 pages.

Extended European Search Report dated Jul. 30, 2018 in 18150967.0, 5 pages.

Bianchini, C., et al., "Cobalt(II) and Nickel(II) Complexes with Tris(2-diethylphosphinoethyl)amine. Crystal and Molecular Structure of the Trinuclear Complex [Ni3(Etnp3)2Cl4](BPH4)2", Inorganica Chimica Acta, vol. 43, 1980, XP055492581, pp. 223-228.

Bianchini, C., et al., "Radial Trinuclear Complexes of Cobalt(II) and Nickel(II) with Tris(2-dimethyiphosphinoethyl)-amine", Inorganica Chimica Acta, vol. 31, Issue 2, Dec. 1978, XP026623205, pp. L433-L434.

Dahlenburg, L., et al., "Oligophosphan-Liganden", Journal of Organometallic Chemistry, vol. 411, Issue 3, Jul. 1991, XP026639028, pp. 457-469.

Fong, H., et al., "Hydricity of an Fe—H Species and Catalytic CO2 Hydrogenation", Inorganic Chemistry, vol. 54, Issue 11, Dec. 31, 2014, XP055492598, pp. 5124-5135.

Fontal, B., et al., "Complejos de Rutenio con fosfinas polidentadas", Acta Cientifica Venezolana, vol. 33, Issue 3, 1982, XP009506569, pp. 202-213.

Hanton. M. J., et al., "Ruthenium-catalysed hydrogenation of esters using tripodal phosphine ligands", Journal of Molecular Catalysis A: Chemical, vol. 346, Issues 1-2, Jul. 20, 2011, XP028258403, pp. 70-78.

Kim, D., et al., "Ester Hydrogenation Catalyzed by CNN-Pincer Complexes of Ruthenium", Organometaliics, vol. 35, Issue 7, Mar. 31, 2016, pp. 982-989.

MacBeth, C. E., et al., "Synthesis and characterization of cationic iron complexes supported by the neutral ligands NPi-Pr3, NArPi-Pr3, and NSt-Bu3", Canadian Journal of Chemistry, vol. 83, Issue 4, 2005, pp. 332-340.

Moran, S., et al., "Chapter 3.3—Reactors for gas-liquid reactions, Reactor Types and Their Industrial Applications", Ullmann's Encyclopedia of Industrial Chemistry, Nov. 22, 2016, pp. 1-49.

Saudan, L. A., et al., "Dihydrogen Reduction of Carboxylic Esters to Alcohols under the Catalysis of Homogeneous Ruthenium Complexes: High Efficiency and Unprecedented Chemoselectivity", Angewandte Chemie International Edition, vol. 46, Issue 39, Sep. 20, 2007, pp. 7473-7476.

Spasyuk, D., et al., "Replacing Phosphorus with Sulfur for the Efficient Hydrogenation of Esters", Angewandte Chemie International Edition, vol. 52, Issue 9, Jan. 28, 2013, pp. 2538-2542.

Teunissen, H. T., et al., "Ruthenium catalysed hydrogenation of dimethyl oxalate to ethylene glycol", Chemical Communications, Issue 7, 1997, pp. 667-668.

Zhang, J., et al., "Efficient Homogeneous Catalytic Hydrogenation of Esters to Alcohols", Angewandte Chemie International Edition, vol. 45, Issue 7, Jan. 30, 2006, pp. 1113-1115.

\* cited by examiner

USE OF A TRANSITION METAL CATALYST COMPRISING A TETRADENTATE LIGAND FOR HYDROGENATION OF ESTERS AND/OR FORMATION OF ESTERS, A PROCESS FOR HYDROGENATION OF ESTERS, A PROCESS FOR FORMATION OF ESTERS AND A TRANSITION METAL COMPLEX COMPRISING SAID TETRADENTATE LIGAND

The present invention relates to the use of a transition metal catalyst TMC1, which comprises a transition metal M selected from metals of groups 7, 8, 9 and 10 of the periodic table of elements according to IUPAC and a tetradentate ligand of formula I

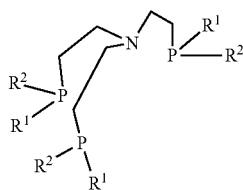

I wherein
$R^1$ are identical or different and are each an organic radical having from 1 to 40 carbon atoms, and
$R^2$ are identical or different and are each an organic radical having from 1 to 40 carbon atoms,
as catalyst in processes for formation of compounds comprising at least one carboxylic acid ester functional group —O—C(=O)— starting from at least one primary alcohol and/or hydrogenation of compounds comprising at least one carboxylic acid ester functional group —O—C(=O)—.

The present invention further relates to a process for hydrogenation of a compound comprising at least one carboxylic acid ester functional group —O—C(=O)—, to a process for the formation of a compound comprising at least one carboxylic acid ester functional group —O—C(=O)— by dehydrogenative coupling of at least one primary alcohol with a second alcoholic OH-group, to a transition metal complex comprising the tetradentate ligand of formula I and to a process for preparing said transition metal complex.

The reduction of carboxylic acid esters to the corresponding alcohols is a fundamental and broadly applied transformation in organic chemistry as well as in industrial applied processes. The most economic approach to reduce an ester functionality to the corresponding alcohols is hydrogenation using molecular hydrogen ($H_2$) in the presence of a catalyst. Also, the dehydrogenative coupling of alcohols to esters is a method to produce esters from alcohols as starting material with molecular hydrogen as the only by-product.

Hydrogenation of Esters:

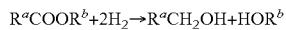

Dehydrogenative Coupling of Alcohols:

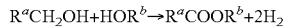

The ideal catalyst system for these reactions should be robust and easy to prepare, and the catalyst system should not need additives, which require dedicated measures for removal after the reaction. Also, the catalyst should be reusable after the reaction without any elaborate catalyst regeneration step. If additives are necessary, ideally, they are already present being the starting material or reaction product formed during the hydrogenation. This would later allow a simpler workup of the product mixture.

In the prior art, active catalyst systems, which perform the hydrogenation of esters were reported using ruthenium with different multidentate ligands. The catalyst systems, which are disclosed in WO2006106484, US20150202609, WO2013023307, U.S. Pat. No. 8,471,048, US2016/0326199, US2017/0073298, EP1868964/65, Angew. Chem. Int. Ed. 2013, 52, 2538-2542, Angew. Chem. Int. Ed. 2006, 45, 1113-1115, Angew. Chem. Int. Ed. 2007, 46, 7473-7476, Chem. Commun. 1997, 667, J. Mol. Catal. 2011, 346, 70 or Organometallics, 2016, 35, 982-989, require the addition of a base to achieve the hydrogenation. The required base is a drawback of these systems, since it must be removed during work-up.

Other catalyst systems in the prior art avoid the use of a base by using preformed catalysts. WO 2016035080, U.S. Pat. No. 8,524,953 and WO 2012052996 disclose ruthenium complexes with tridentate pincer type ligands. These complexes can be used as catalysts for both above-described reactions without the presence of an additional base. The ruthenium complex bears eithers an anionic $BH_4$-ligand or is deprotonated in a previous synthetic step. A drawback of these catalyst systems is, that they are prepared in four to five step synthesis starting from commercially available starting materials. In addition, the $BH_4^-$-anion as well as the deprotonated active catalyst are relatively sensitive towards water and air. These catalysts also protolyze during the reaction by the formed alcohol. Therefore, catalyst recycling of these complexes without adding a new $BH_4$-source or a base has not been achieved so far in the prior art. For an economic process, it is essential, that the catalyst system can be recycled.

The preparation of complexes of ruthenium with polydentate ligands including $N(CH_2CH_2PPh_2)_3$ were disclosed in Acta Cient. Venezolana 33, 202-213, 1982.

Proceeding from this prior art, an object of the invention was to provide a robust catalyst system for the above-described hydrogenation of carboxylic esters or the dehydrogenative coupling of alcohols to carboxylic esters in an economically advantageous manner.

This object is achieved by the use of a transition metal catalyst TMC1, which comprises a transition metal M selected from metals of groups 7, 8, 9 and 10 of the periodic table of elements according to IUPAC and a tetradentate ligand of formula I

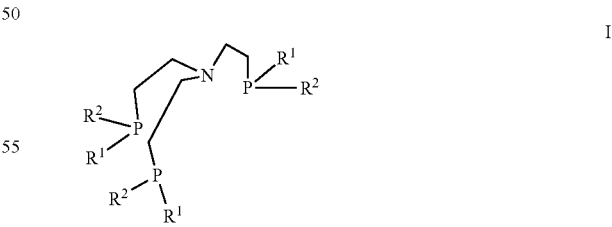

I wherein
$R^1$ are identical or different and are each an organic radical having from 1 to 40 carbon atoms, and
$R^2$ are identical or different and are each an organic radical having from 1 to 40 carbon atoms,
as catalyst in processes for formation of compounds comprising at least one carboxylic acid ester functional group —O—C(=O)— starting from at least one primary alcohol and/or hydrogenation of compounds comprising at least one carboxylic acid ester functional group —O—C(=O)—.

The substituents according to the present invention are, unless restricted further, defined as follows:

The term "organic radical having from 1 to 40 carbon atoms" as used in the present text refers to, for example, $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, silyl radicals having from 3 to 24 carbon atoms, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C$—), methoxy ($H_3C$—O—) and hydroxymethyl ($HOC(H_2)$—). Therefore, the term "organic radical having from 1 to 40 carbon atoms" comprises besides alkoxy radicals for example also dialkylamino radicals, monoalkylamino radicals or alkylthio radicals.

In the present description, the term radical is used interchangeably with the term group, when defining the variables $R^x$ in the presented formulas.

The term "alkyl" as used in the present text encompasses linear or singly or multiply branched saturated hydrocarbons which can also be cyclic. Preference is given to a $C_1$-$C_{18}$-alkyl radical such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having one or more C—C double bonds which can be cumulated or alternating.

The term "saturated heterocyclic radical" as used in the present text refers to, for example, monocyclic or polycyclic, substituted or unsubstituted aliphatic or partially unsaturated hydrocarbon radicals in which one or more carbon atoms, CH groups and/or $CH_2$ groups have been replaced by heteroatoms which are preferably selected from the group consisting of the elements O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydro thienyl and the like, and also methyl-, ethyl-, propyl-, isopropyl- and tert-butyl-substituted derivatives thereof. In the present application the term "heterocycloalkyl radical" is used for those saturated heterocyclic radicals, which are substituted or unsubstituted aliphatic hydrocarbon radicals in which one or more carbon atoms, CH groups and/or $CH_2$ groups have been replaced by heteroatoms which are preferably selected from the group consisting of the elements O, S, N and P as described above.

The term "aryl" as used in the present text refers to, for example, aromatic and optionally fused polyaromatic hydrocarbon radicals which may be monosubstituted or polysubstituted by linear or branched $C_1$-$C_{18}$-alkyl, $C_1$-$C_{18}$-alkoxy, $C_2$-$C_{10}$-alkenyl, halogen, in particular fluorine, or functional groups such as COOH, hydroxy, $NH_2$, mercapto or $SO_3H$. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers to, for example, aromatic hydrocarbon radicals in which one or more carbon atoms or CH groups have been replaced by nitrogen, phosphorus, oxygen or sulfur atoms or combinations thereof. These may, like the aryl radicals, optionally be monosubstituted or polysubstituted by linear or branched $C_1$-$C_{18}$-alkyl, $C_2$-$C_{10}$-alkenyl, halogen, in particular fluorine, or functional groups such as COOH, hydroxy, $NH_2$, mercapto or $SO_3H$. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers to, for example, aryl-comprising substituents where the corresponding aryl radical is linked via an alkyl chain to the rest of the molecule. Preferred examples are benzyl, substituted benzyl, phenethyl, substituted phenethyl and related structures.

The terms fluoroalkyl and fluoroaryl mean that at least one hydrogen atom, preferably more than one and ideally all hydrogen atoms, of the corresponding radical have been replaced by fluorine atoms. Examples of preferred fluorine-comprising radicals are trifluoromethyl, 2,2,2-trifluoroethyl, pentafluorophenyl, 4-trifluoromethylphenyl, 4-perfluoro-tert-butylphenyl and related structures.

The transition metal catalyst TMC1 can comprise besides the tetradentate ligand of formula I one or more additional ligands, such as an anion selected from the group consisting of hydride, alkoxides, aryloxides, carboxylates and acyl, or a neutral ligand selected from the group consisting of carbon monoxide, triaryl phosphines, amines, N-heterocyclic carbenes and isonitriles. Preferably the transition metal catalyst TMC1 further comprises a carbon monoxide ligand.

In one embodiment of the present invention, the inventive use is characterized in that the transition metal catalyst TMC1 further comprises a carbon monoxide ligand.

In one embodiment of the present invention, the inventive use is characterized in that the transition metal catalyst TMC1 is a transition metal complex of formula

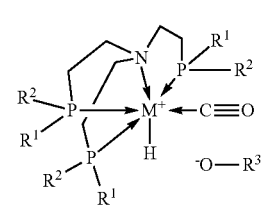

II wherein
M is a transition metal selected from metals of groups 7, 8, 9 and 10 of the periodic table of elements according to IUPAC,
$R^1$ are identical or different and are each an organic radical having from 1 to 40 carbon atoms,
$R^2$ are identical or different and are each an organic radical having from 1 to 40 carbon atoms, and
$R^3$ is hydrogen or an organic radical having from 1 to 40 carbon atoms which is bound via a carbon atom to the oxygen atom, preferably $R^3$ is an organic radical having from 1 to 40 carbon atoms which is bound via a carbon atom to the oxygen atom,
or $R^3$ together with $R^1$ or $R^3$ together with $R^2$, together with the atoms connecting them, form a divalent organic group having from 1 to 40 carbon atoms.

The transition metal M of transition metal catalyst TMC1 and of the transition metal complex of formula II is selected from metals of groups 7, 8, 9 and 10, preferably selected from metals of groups 8, 9 and 10, of the periodic table of elements according to IUPAC, preferably selected from the metal consisting of iron, cobalt, nickel, ruthenium, rhodium, palladium, osmium, iridium and platinum, in particular ruthenium.

In one embodiment of the present invention, the inventive use is characterized in that the transition metal M is ruthenium.

While in formula I and accordingly in formula II, the three radicals $R^1$ are identical or different, preferably identical, and the three radicals $R^2$ are identical or different, preferably identical, two radicals $R^1$ and $R^2$, which are both attached to the same phosphorus atom, are again identical or different, preferably identical. The six radicals $R^1$ and $R^2$ in formula I and accordingly in formula II might represent up to 6 different radicals. Preferably all six radicals $R^1$ and $R^2$ are identical.

In one embodiment of the present invention, the inventive use is characterized in that $R^1$ and $R^2$ are identical.

In one embodiment of the present invention, the inventive use is characterized in that $R^1$ are identical or different, preferably identical, and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, preferably a $C_6$ to $C_{40}$ aryl radical or a $C_2$ to $C_{40}$ heteroaromatic radical, which can be substituted at any position with a radical which is an organic radical having from 1 to 40 carbon atoms, a halogen, preferably F, Cl or Br, in particular F, or COOH, hydroxy, $NH_2$, mercapto or $SO_3H$, and $R^2$ are identical or different, preferably identical, and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, preferably a $C_6$ to $C_{40}$ aryl radical or a $C_2$ to $C_{40}$ heteroaromatic radical, which can be substituted at any position with a radical which is an organic radical having from 1 to 40 carbon atoms, a halogen, preferably F, Cl or Br, in particular F, or COOH, hydroxy, $NH_2$, mercapto or $SO_3H$.

Preferably $R^1$ and $R^2$ are identical and are methyl, ethyl, 1-propyl, 2-propyl, 1-butyl, 1-hexyl, 1-octyl-iso-butyl, adamantyl, 2-pyridyl, 3-pyridyl, 4-pyridyl, cyclohexyl, cyclopentyl, tert.-butyl, p-tert.-butyl-phenyl, o-tolyl, m-tolyl, p-tolyl, p-methoxy-phenyl, p-trifluoromethyl-phenyl, 4-biphenyl, naphthyl or phenyl, in particular phenyl.

The radical $R^3$ in formula II is hydrogen or an organic radical having from 1 to 40 carbon atoms which is bound via a carbon atom to the oxygen atom. Preferably the radical $R^3$ in formula II is an organic radical having from 1 to 40 carbon atoms which is bound via a carbon atom to the oxygen atom. More preferably the anion $^-OR^3$ represents an alcoholate or a carboxylate ion.

In one embodiment of the present invention, the inventive use is characterized in that $R^3$ is a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical, a C to $C_{40}$ arylalkyl radical or a $C_2$ to $C_{40}$ heteroaromatic radical, or $R^3$ is $C(=O)R^4$, wherein $R^4$ is hydrogen, a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical, a $C_7$ to $C_{40}$ arylalkyl radical or a $C_2$ to $C_{40}$ heteroaromatic radical.

Preferably $R^3$ is a $C_1$ to $C_6$ alkyl radical such as methyl, ethyl, isopropyl, cyclohexyl, cyclopentyl, tert.-butyl, or a substituted or unsubstituted $C_6$ to $C_1$ aryl radical such as p-tert.-butyl-phenyl, o-tolyl, m-tolyl, p-toly, naphthyl, phenyl, or a substituted or unsubstituted C to $C_1$, arylalkyl radical such as benzyl, a $C_1$ to $C_{15}$ alkanoyl radical, such as formyl, acetyl, propionyl, or substituted or unsubstituted benzoyl.

In one embodiment the present invention relates to the use of a transition metal catalyst TMC1, which comprises a transition metal M selected from metals of groups 7, 8, 9 and 10 of the periodic table of elements according to IUPAC and a tetradentate ligand of formula I

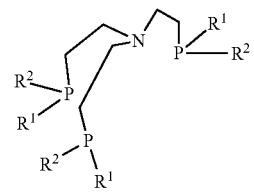

I wherein
$R^1$ are identical or different and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, and $R^2$ are identical or different and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, and, wherein the transition metal M is ruthenium and wherein the transition metal catalyst TMC1 further comprises a carbon monoxide ligand, as catalyst in processes for formation of compounds comprising at least one carboxylic acid ester functional group —O—C(=O)— starting from at least one primary alcohol and/or hydrogenation of compounds comprising at least one carboxylic acid ester functional group —O—C(=O)—.

In another embodiment of the present invention, the inventive use is characterized in that the transition metal catalyst TMC1 is a transition metal complex of formula II

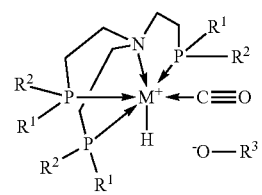

II wherein M, $R^1$ and $R^2$ are defined as described above and
$R^3$ is a $C_1$ to $C_{40}$ alkyl radical, a $C_3$ to $C_{40}$ cycloalkyl radical, a $C_2$ to $C_{40}$ heterocy-cloalkyl radical, a $C_6$ to $C_{40}$ aryl radical, a C to $C_{40}$ arylalkyl radical or a $C_2$ to $C_{40}$ heteroaromatic radical, or $R^3$ is $C(=O)R^4$, wherein $R^4$ is hydrogen, a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical, a C to $C_{40}$ arylalkyl radical or a $C_2$ to $C_{40}$ heteroaromatic radical, which in each case is bound via a carbon atom to the oxygen atom, or R³ together with R¹ or R³ together with R², together with the atoms connecting them, form a divalent organic group having from 1 to 40 carbon atoms.

The above-described transition metal catalyst TMC1, which comprises the tetradentate ligand of formula I, can be used in processes for formation of compounds comprising at least one carboxylic acid ester functional group —O—C(=O)— starting from at least one primary alcohol and/or hydrogenation of compounds comprising at least one carboxylic acid ester functional group —O—C(=O)— in the presence of additional bases or without additional bases. An advantage of above-described transition metal catalyst TMC1 compared with transition metal catalyst of the literature is the fact that TMC1 can be used in the above-mentioned processes without the need of additional bases, such as alkali metal or alkaline earth metal carbonates, alkali metal or alkaline earth metal hydroxides and alkali metal or alkaline earth metal alcoholates. Furthermore, a base-free catalyst enables the hydrogenation of base-labile substrates (possibly chiral α-substituted esters).

In one embodiment of the present invention, the inventive use is characterized in that no base selected from the group consisting of alkali metal or alkaline earth metal carbonates, alkali metal or alkaline earth metal hydroxides and alkali metal or alkaline earth metal alcoholates is combined with the transition metal catalyst TMC1.

The amount of the transition metal catalyst TMC1, which is applied for practicing the inventive use can be varied in a wide range. Preferably, the amount of transition metal catalyst TMC1, which is used in the hydrogenation of esters as well as the dehydrogenative coupling of alcohols, is in the range from 0.1 to 5000 ppm (parts per weight), more preferably in the range from 1 to 2000 ppm, in particular in the range from 50 to 1000 ppm, in each case based on the total weight of the liquid reaction mixture.

In one embodiment of the present invention, the inventive use is characterized in that the catalyzed reactions take place in a homogenous liquid reaction phase. That means, that the hydrogenation of carboxylic acid esters and the formation of carboxylic acid esters starting from at least one primary alcohol by dehydrogenative coupling are preferably homogenous processes.

A further aspect of the invention relates to a process for hydrogenation of a compound comprising at least one carboxylic acid ester functional group —O—C(=O)— to the corresponding compound or compounds each comprising at least one alcoholic hydroxy group,
comprising the process step:
a) treating said compound, which comprises at least one carboxylic acid ester functional group —O—C(=O)—, with molecular hydrogen $H_2$ in the presence of a catalytic amount of a transition metal catalyst TMC1, which comprises a transition metal M selected from metals of groups 7, 8, 9 and 10 of the periodic table of elements according to IUPAC and a tetradentate ligand of formula I, wherein TMC1 M and the tetradentate ligand of formula I are defined as described above, including preferred embodiments of said transition metal catalyst TMC1 and its components.

In the sense of the invention, the term compounds comprising at least one carboxylic acid ester functional group —O—C(=O)— refers to carboxylic acid esters.

In the sense of the invention, examples of a compound comprising at least one carboxylic acid ester functional group —O—C(=O)—, are: monocarboxylic acid esters such as ethyl acetate, n-hexyl hexanoate, isopropyl benzoate or benzyl stearate; cyclic monocarboxylic acid esters, also called lactones, such as γ-butyrolactone, δ-valerolactone, ε-caprolactone or sclareolide; dicarboxylic acid esters such as diethyl malonate, dimethyl terephthalate, ethylene glycol diacetate or 1,4-diacetoxybutane; cyclic dicarboxylic acid esters like lactide or glycolide; tricarboxylic acid esters such as triethyl citrate or triacylglycerides of fatty acids; or oligo- or polycarboxylic acid esters such as polybutylene terephthalate (PBT), polyethylene terephthalate (PET), polyethylene naphthalate or polylactide.

In the sense of the invention, the compound or compounds each comprising at least one alcoholic hydroxy group refer to alcohols or phenols. The part of the ester originating from the carboxylic acid is hydrogenated to a primary alcohol (—CH₂—OH) while the part of the ester originating from alcohol or phenol produces the respective alcohol or phenol.

In one embodiment of the present invention, the inventive process for hydrogenation of a compound comprising at least one carboxylic acid ester functional group —O—C(=O)— is characterized in that the compound comprising at least one carboxylic acid ester functional group —O—C(=O)— is a compound of formula III

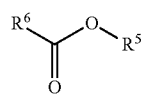

III wherein
R⁵ is an organic radical having from 1 to 40 carbon atoms, which is bound via a carbon atom to the oxygen atom, and
R⁶ is hydrogen or an organic radical having from 1 to 40 carbon atoms, which is bound via a carbon atom to the carbonyl group
or R⁵ and R⁶ together with the atoms connecting them form a divalent organic group having from 1 to 40 carbon atoms.

As explained above, the compound of formula III might comprise one or more additional carboxylic acid ester functional groups, which is/are part of R⁵ and/or of R⁶. Preferably, R⁵ is a $C_1$ to $C_{40}$ alkyl radical, a $C_2$ to $C_{40}$ alkenyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, and R⁶ is hydrogen, a $C_1$ to $C_{40}$ alkyl radical, a $C_2$ to $C_{40}$ alkenyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, wherein R⁵ and R⁶ can be substituted at any position with a radical which is an organic radical having from 1 to 40 carbon atoms, an ester function, a halogen, in particular F, C or Br, COOH, hydroxy, $NH_2$, mercapto or $SO_3H$.

In one embodiment R⁵ in formula III is a $C_1$ to $C_{40}$ alkyl radical, preferably methyl, ethyl, propyl, isopropyl or butyl.

In one embodiment R⁶ in formula III is substituted by one or more additional groups —C(=O)OR⁵, preferably one additional group —C(=O)OR⁵. Examples of such diesters of formula III derived from dicarboxylic acids, such as terephthalic acid, phthalic acids, maleic acid, adipic acid or succinic acid, are preferably di esters, wherein R⁵ is in particular methyl, ethyl, propyl, isopropyl, butyl or isobutyl, for example dimethyl terephthalate (terephthalic acid dimethyl ester).

In one embodiment R⁵ and R⁶ together with the atoms connecting them form a divalent organic group having from 1 to 40 carbon atoms. Examples of cyclic monoesters of formula III are lactones such as γ-butyrolactone, δ-valerolactone, ε-caprolactone or sclareolide. Examples of cyclic di-esters of formula III are glycolide, the cyclic di-ester of glycolic acid, or lactide, the cyclic di-ester of lactic acid.

In one embodiment of the present invention, the inventive process for hydrogenation of a compound comprising at least one ester functional group is characterized in that an alcohol or a carboxylic acid, preferably an alcohol, is added to the reaction mixture, which comprises the compound comprising at least one ester functional group and the transition metal catalyst TMC1 before starting the hydrogenation reaction of process step a). The added alcohol can be varied in a wide range. Preferably the added alcohol can be defined as $R^3$—OH, $R^5$—OH or $R^6$—CH$_2$—OH, wherein $R^3$, $R^5$ and $R^6$ are defined as described above. The addition of an alcohol, which is the same as one of the alcohols formed in the ester hydrogenation, simplifies the workup of the final product mixture of the hydrogenation reaction. The added alcohol or carboxylic acid, preferably the alcohol, serves as activator of the transition metal catalyst TMC1.

The amount of alcohol or carboxylic acid added to the reaction mixture, preferably alcohol, can be varied in a wide range. Preferably the amount of alcohol or carboxylic acid added, preferably alcohol, ranges from 0.001 to 90 wt.-%, more preferably from 0.01 to 10 wt.-%, in particular from 0.01 to 5 wt.-%, in each case based on the total weight of the liquid reaction mixture.

As already mentioned above, the transition metal catalyst TMC1 can be used in processes for formation of compounds comprising at least one carboxylic acid ester functional group —O—C(=O)— starting from at least one primary alcohol and/or hydrogenation of compounds comprising at least one carboxylic acid ester functional group —O—C(=O)— in the presence of additional bases or without additional bases, such as alkali metal or alkaline earth metal carbonates, alkali metal or alkaline earth metal hydroxides and alkali metal or alkaline earth metal alcoholates. Even though, the addition of said bases improves the activity of transition metal catalyst TMC1 but the performance of the transition metal catalyst TMC1 is still satisfying even without adding a base. Avoiding the addition of said bases to the reaction mixture of process step a) prevents extra work during isolation of the desired product and also base labile substrates (e.g. esters of α-chiral carboxylic acids) can be used.

In one embodiment of the present invention, the inventive process for hydrogenation of a compound comprising at least one carboxylic acid ester functional group is characterized in that no base selected from the group consisting of alkali metal or alkaline earth metal carbonates, alkali metal or alkaline earth metal hydroxides and alkali metal or alkaline earth metal alcoholates is added to the reaction mixture of process step a).

The inventive process for hydrogenation of a compound comprising at least one ester functional group works in a broad temperature range. Preferably the ester hydrogenation takes place at a temperature in the range from 20 to 250° C. More preferably, the process according to the invention is carried out at temperatures in the range from 70 to 200° C., in particular in the range from 80 to 150° C.

As explained above, for the reduction of each carboxylic acid ester functional group two equivalents of molecular hydrogen (2 H$_2$) are consumed. During the inventive process for hydrogenation the hydrogen pressure can be varied in a wide range. Preferably, the ester hydrogenation takes place at hydrogen pressures in the range from 0.1 to 50 MPa, more preferably at hydrogen pressures in the range from 1 to 20 MPa, in particular in the range from 3 to 15 MPa.

The inventive process for hydrogenation of a compound comprising at least one ester functional group can be carried out in the customary devices and/or reactors known to the person skilled in the art for liquid-gas reactions in which the catalyst is present in the liquid phase. For the inventive process, it is in principle possible to use all reactors which are fundamentally suitable for gas-liquid reactions under the stated temperatures and the stated pressures. Suitable standard reactors for gas-liquid and for liquid-liquid reaction systems are discussed for example in K. Henkel, "Reactor Types and Their Industrial Applications", Ullmann's Encyclopedia of Industrial Chemistry, 2005, Wiley-VCH Verlag GmbH & Co. KGaA, chapter 3.3: "Reactors for gas-liquid reactions", to which reference is hereby made. Examples which may be mentioned are stirred tank reactors, tubular reactors or bubble column reactors. The supply of ester, catalyst, solvent and optionally an alcohol as activator can take place here simultaneously or separately from one another. The reaction here can be carried out discontinuously in batch mode or continuously, semi-continuously with recycle or without recycle. The average residence time in the reaction space can be varied in a wide range, preferably in the range from 15 minutes to 100 h, more preferably in the range from 1 h to 50 h.

The inventive process for hydrogenation of a compound comprising at least one ester functional group can be carried out in the absence of any solvent but also in the presence of a solvent. Suitable solvents are selected from aliphatic hydrocarbons, aromatic hydrocarbons, alcohols, esters, ethers, water and mixtures thereof. Preferred solvents are
  aliphatic hydrocarbons such as pentane, hexane, heptane, octane or cyclohexane;
  aromatic hydrocarbons such as benzene, toluene, xylenes, ethylbenzene, mesitylene or benzotrifluoride;
  alcohols such as methanol, ethanol, propanol or isopropanol;
  ethers such as dioxane, tetrahydrofuran, diethyl ether, dibutyl ether, methyl t-butyl ether, diisopropyl ether or diethylene glycol dimethyl ether and water.

If desired, mixtures of two or more of the afore-mentioned solvents can also be used.

Preference is given to using aliphatic hydrocarbons, aromatic hydrocarbons, ethers and mixtures thereof as solvents.

In one embodiment of the present invention, the inventive process for hydrogenation of a compound comprising at least one ester functional group is characterized in that process step a) is carried out in the presence of a solvent selected from aliphatic hydrocarbons, aromatic hydrocarbons, alcohols, esters, ethers, water and mixtures thereof.

The work-up of the reaction mixture obtained after finishing process step a), in particular the isolation of the formed alcohols, in particular $R^6CH_2OH$ and $R^5OH$ can be realized case dependent, for example by filtration, an aqueous extractive work-up or by distillation as separation method, for example distillation under reduced pressure. Preferably the work up is performed by distillation and the catalyst remains in the residue of the distillation to allow recycling.

A further aspect of the invention relates to a process for the formation of a compound of formula III comprising at least one carboxylic acid ester functional group —O—C(=O)

III

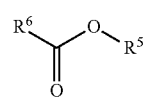

by dehydrogenative coupling of at least one primary alcohol of formula IV comprising at least one hydroxy methylene group

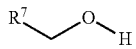

IV with a second primary alcohol of formula IV, or
intramolecularly, if present, with a second alcoholic OH group of the primary alcohol of formula IV, or
with an alcohol of formula V comprising at least one alcoholic hydroxyl group

V wherein
$R^5$ is an organic radical having from 1 to 40 carbon atoms, which is bound via a carbon atom to the hydroxy group,
$R^6$ is hydrogen or an organic radical having from 1 to 40 carbon atoms, which is bound via a carbon atom to the carbonyl group,
$R^7$ is hydrogen or an organic radical having from 1 to 40 carbon atoms, which is bound via a carbon atom to the hydroxy methylene group,
or $R^5$ and $R^6$ together with the atoms connecting them form a divalent organic group having from 1 to 40 carbon atoms,
comprising the process step:
b) treating said primary alcohol of formula IV alone or in a mixture with said alcohol of formula V with a catalytic amount of a transition metal catalyst TMC1, which comprises a transition metal M selected from metals of groups 7, 8, 9 and 10 of the periodic table of elements according to IUPAC and a tetradentate ligand of formula I, wherein TMC1, M and the tetradentate ligand of formula I are defined as described above, including preferred embodiments of said transition metal catalyst TMC1 and its components.

In principle, the compound of formula III together with its variables $R^5$ and $R^6$ and consequently also the compound of formula V with its variable $R^5$ are defined as described above in the case of the process for hydrogenation of the compound of formula III comprising at least one carboxylic acid ester functional group —O—C(=O)—. As described above, the compound of formula III can be a monocarboxylic acid ester including a lactone, a dicarboxylic acid ester including a dilactone, tricarboxylic acid ester or even a, oligo- or polycarboxylic acid ester. Preferably, the compound of formula III formed in the dehydrogenative coupling process is a monocarboxylic acid ester.

Whereas the complete hydrogenation of all carboxylic acid ester groups of a single ester of formula III results in the formation of a limited number of alcohols, the dehydrogenative coupling of at least one primary alcohol of formula IV comprising at least one hydroxy methylene group with at least one alcohol of formula V comprising at least one alcoholic hydroxyl group is limited in view of the preferred formation of a single ester of formula III. A single primary alcohol, such as n-pentanol can form only one monoester, while two different primary alcohols, such as a 1:1 mixture of n-pentanol and n-hexanol, can form four different esters.

In one embodiment of the present invention, the inventive process for the formation of a compound of formula III comprising at least one, preferably only one carboxylic acid ester functional group —O—C(=O)— is characterized in that two molecules of the primary alcohol of formula IV, preferably comprising only one alcoholic OH group, react with each other.

In one embodiment $R^5$ in formula III is a $C_1$ to $C_{40}$ alkyl radical, preferably a $C_1$ to $C_{18}$, n-alkylradical, more preferably methyl, ethyl, n-propyl, n-butyl, n-pentyl, n-hexyl, n-octyl, n-decyl, n-dodecyl, n-tetradecyl, n-hexadecyl or n-octadecylanol.

In one embodiment of the present invention, the inventive process for dehydrogenative coupling is characterized in that the alcohol of formula V is identical with the primary alcohol of formula IV and the primary alcohol of formula IV is selected from the group of alcohols consisting of methanol, ethanol, 1-propanol, 1-butanol, 1-pentanol, 1-hexanol, 1-octanol, 1-decanol, 1-dodecanol, 1-tetradecanol, 1-hexadecanol and 1-octadecanol.

As already mentioned above, the transition metal catalyst TMC1 can be used in processes for formation of compounds comprising at least one carboxylic acid ester functional group —O—C(=O)— starting from at least one primary alcohol and/or hydrogenation of compounds comprising at least one carboxylic acid ester functional group —O—C(=O)— in the presence of additional bases or without additional bases, such as alkali metal or alkaline earth metal carbonates, alkali metal or alkaline earth metal hydroxides and alkali metal or alkaline earth metal alcoholates. Even though, the addition of said bases improves the activity of transition metal catalyst TMC1, but the performance of the transition metal catalyst TMC1 is still satisfying even without adding a base. Avoiding the addition of said bases to the reaction mixture of process step a) prevents extra work during isolation of the desired product and also base labile substrates (e.g. esters of α-chiral carboxylic acids) can be used.

In one embodiment of the present invention, the inventive process for dehydrogenative coupling of at least one primary alcohol of formula IV with at least one alcohol of formula V to at least one ester of formula III is characterized in that no base selected from the group consisting of alkali metal or alkaline earth metal carbonates, alkali metal or alkaline earth metal hydroxides and al kali metal or alkaline earth metal alcoholates is added to the reaction mixture of process step b).

The inventive process for dehydrogenative coupling as described above works in a broad temperature range. Preferably the dehydrogenative coupling of alcohols takes place at a temperature in the range from 20 to 250° C. More preferably, the process according to the invention is carried out at temperatures in the range from 70 to 200° C., in particular in the range from 80 to 180° C.

During the dehydrogenative coupling as describe above for each formed carboxylic acid ester functional group two equivalents of molecular hydrogen (2 $H_2$) are produced. In order to complete the dehydrogenative coupling, the formed molecular hydrogen ($H_2$) is preferably removed from the reaction mixture, in order to avoid the reverse reaction, that is the hydrogenation of the carboxylic acid ester functional group. This is performed either by stripping out with the boiling unreacted alcohol or by introducing a stripping gas such as nitrogen, carbon dioxide or argon.

During the dehydrogenative coupling the overall pressure, of which the partial pressure of molecular hydrogen is only one component, can be varied in a wide range. Preferably the dehydrogenative coupling of alcohols takes place at overall pressures in the range from 0.001 to 10 MPa. More preferably, the process according to the invention is carried out at overall pressures in the range from 0.001 to 1 MPa, in particular in the range from 0.001 to 0.2 MPa.

The inventive process for dehydrogenative coupling as describe above can be carried out in the customary devices and/or reactors known to the person skilled in the art of liquid-gas reaction in which the catalyst is present in the liquid phase. For the inventive, it is in principle possible to use all reactors which are fundamentally suitable for gas-liquid reactions under the stated temperature and the stated pressure. Suitable standard reactors for gas-liquid and for liquid-liquid reaction systems are discussed for example in K. Henkel, "Reactor Types and Their Industrial Applications", Ullmann's Encyclopedia of Industrial Chemistry, 2005, Wiley-VCH Verlag GmbH & Co. KGaA, chapter 3.3: "Reactors for gas-liquid reactions", to which reference is hereby made. Examples which may be mentioned are stirred tank reactors, tubular reactors or bubble column reactors. The supply of alcohols, catalyst I and solvent can take place here simultaneously or separately from one another. The reaction here can be carried out discontinuously in batch mode or continuously, semi-continuously with recycle or without recycle. The average residence time in the reaction space is generally 15 minutes to 100 h, in particular 1 h to 50 h.

The inventive process for dehydrogenative coupling of alcohols can be carried neat but also in the presence of a solvent. Suitable solvents are selected from aliphatic hydrocarbons, aromatic hydrocarbons, esters, ethers, and mixtures thereof. Preferred solvents are aliphatic hydrocarbons such as pentane, hexane, heptane, octane or cyclohexane;

aromatic hydrocarbons such as benzene, toluene, xylenes, ethylbenzene, mesitylene or benzotrifluoride;

esters such as methyl acetate, ethyl acetate, t-butyl acetate;

ketones such as acetone and cyclohexanone ethers such as dioxane, tetrahydrofuran, diethyl ether, dibutyl ether, methyl t-butyl ether, diisopropyl ether or diethylene glycol dimethyl ether;

If desired, mixtures of two or more of the afore-mentioned solvents can also be used.

Preference is given to using aliphatic hydrocarbons, aromatic hydrocarbons, ethers and mixtures thereof as solvents.

In one embodiment of the present invention, the inventive process is characterized in that the reaction is carried out in the presence of a solvent selected from aliphatic hydrocarbons, aromatic hydrocarbons, ethers and mixtures thereof.

The work-up of the reaction mixture obtained in the inventive process for dehydrogenative coupling of alcohols and the isolation of the esters are performed in a customary manner, for example by filtration, an aqueous extractive work-up or by distillation as separation method, for example under reduced pressure. The ester is obtained in sufficient purity by applying such measures or a combination thereof, preventing additional purification steps. Alternatively, further purification can be accomplished by methods commonly used in the art, such as chromatography. Preferably the work-up is performed by distillation and the catalyst remains in the residue of the distillation to allow recycling of transition metal catalyst TMC1.

A further aspect of the invention relates to a transition metal complex of formula

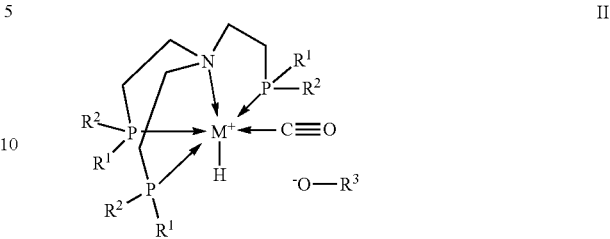

II wherein M, $R^1$, $R^2$ and $R^3$ are defined as described above, that means

M is a transition metal selected from metals of groups 7, 8, 9 and 10 of the periodic table of elements according to IUPAC, in particular ruthenium, $R^1$ are identical or different and are each hydrogen or an organic radical having from 1 to 40 carbon atoms, in particular are identical or different and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, $R^2$ are identical or different and are each hydrogen or an organic radical having from 1 to 40 carbon atoms, in particular are identical or different and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, and $R^3$ is an organic radical having from 1 to 40 carbon atoms which is bound via a carbon atom to the oxygen atom, in particular is a $C_1$ to $C_{40}$ alkyl radical, a $C_3$ to $C_{40}$ cycloalkyl radical, a $C_2$ to $C_{40}$ heterocy-cloalkyl radical, a $C_6$ to $C_{40}$ aryl radical, a $C_7$ to $C_{40}$ arylalkyl radical or a $C_2$ to $C_{40}$ heteroaromatic radical, or $R^3$ is $C(=O)R^4$, wherein $R^4$ is hydrogen, a $C_1$ to $C_{40}$ alkyl radical, a $C_3$ to $C_{40}$ cycloalkyl radical, a $C_2$ to $C_{40}$ heterocycloalkyl radical, a $C_6$ to $C_4$ aryl radical, a $C_7$ to $C_{40}$ arylalkyl radical or a $C_2$ to $C_{40}$ heteroaromatic radical, which in each case is bound via a carbon atom to the oxygen atom, or $R^3$ together with $R^1$ or $R^3$ together with $R^2$, together with the atoms connecting them, form a divalent organic group having from 1 to 40 carbon atoms, where preferred embodiments of said variables M, $R^1$, $R^2$ and $R^3$ have been described above.

In one embodiment of the invention, the inventive transition metal complex of formula II is characterized in that M is ruthenium (Ru), $R^1$ are identical and are each methyl, ethyl, 1-propyl, 2-propyl, 1-butyl, 1-hexyl, 1-octyl-isobutyl, adamantyl, 2-pyridyl, 3-pyridyl, 4-pyridyl, cyclohexyl, cyclopentyl, tert.-butyl, p-tert.butyl-phenyl, o-tolyl, m-tolyl, p-tolyl, p-methoxy-phenyl, p-trifluoromethyl-phenyl, 4-biphenyl, or phenyl, in particular phenyl, $R^2$ are identical and are each methyl, ethyl, 1-propyl, 2-propyl, 1-butyl, 1-hexyl, 1-octyl-isobutyl, adamantyl, 2-pyridyl, 3-pyridyl, 4-pyridyl, cyclohexyl, cyclopentyl, tert.-butyl, p-tert.butyl-phenyl, o-tolyl, m-tolyl, p-tolyl, p-methoxy-phenyl, p-trifluoromethyl-phenyl, 4-biphenyl, or phenyl, in particular phenyl, $R^3$ is $C_1$ to $C_{18}$ alkyl, preferably $C_1$ to $C_6$ alkyl, more preferably methyl, ethyl, isopropyl, cyclohexyl, cyclopentyl or tert.-butyl, substituted or unsubstituted $C_6$ to $C_{18}$ aryl, preferably p-tert.-butyl-phenyl, o-tolyl, m-tolyl, p-toly, naphtyl or phenyl, substituted or unsubstituted C to $C_{18}$ arylalkyl, preferably benzyl, a $C_1$ to $C_{15}$ alkanoyl radical, preferably formyl, acetyl, propionyl, or a substituted or unsubstituted $C_6$ to $C_{15}$ aroyl radical, preferably benzoyl, wherein $R^1$ and $R^2$ are identical.

The tetradentate ligand of formula I

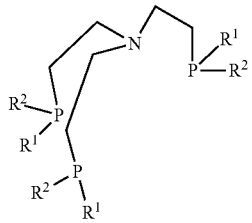

I wherein $R^1$ and $R^2$ are defined as described above, that means $R^1$ are identical or different and are each an organic radical having from 1 to 40 carbon atoms, in particular are identical or different and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, and $R^2$ are identical or different and are each an organic radical having from 1 to 40 carbon atoms, in particular are identical or different and are each a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, wherein preferred embodiments of said variables $R^1$ and $R^2$ have been described above, can be prepared as shown in case of the preparation of ligand L, which can for example be synthesized from tris(2-chloroethyl)amine hydrochloride, diphenylphosphine and potassium tertbutoxide.

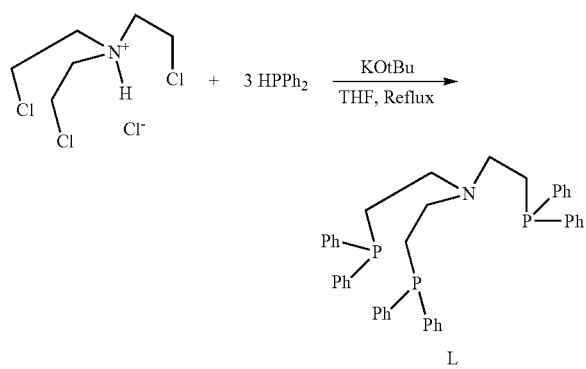

L

Suitable phosphines are commercially available. Alternative phosphines $HPR^1R^2$, that could be used instead of $HPPh_2$ are for example $HPMe_2$, $HPEt_2$, $HPiPr_2$, $HP(cy-Hex)_2$, $HP(cy-Pent)2$, $HP(t-Bu)_2$, $HP(o-tolyl)_2$, $HP(m-tolyl)_2$ or $HP(p-tolyl)_2$. Most preferred is $HPPh_2$.

A further aspect of the invention relates to a process for preparing the transition metal complex of formula II

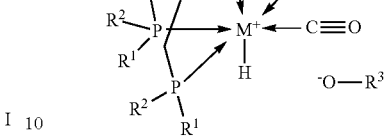

II as described above,
comprising the process step:
c) contacting a transition metal compound of formula VI

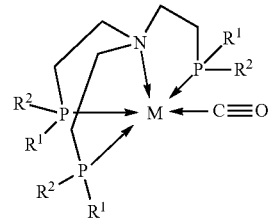

VI with a compound of formula VII,

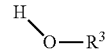

VII wherein the variables M, $R^1$, $R^2$ and $R^3$ are defined as described above, including preferred embodiments of said variables.

In one embodiment of the invention, the inventive process for preparing the transition metal complex of formula II is characterized in that the transition metal compound of formula VI and the compound of formula VII are contacted in a liquid phase.

In one embodiment of the invention, the inventive process for preparing the transition metal complex of formula II is characterized in that the transition metal compound of formula VI with $R^2$ and $R^1$=phenyl is used.

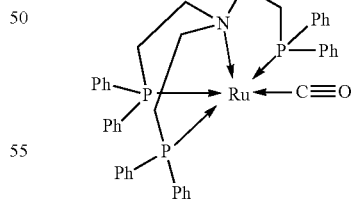

Process step c) can be done independently of process step a) or process step b) or process step c) takes place while performing process step a) or process step b), that means the transition metal complex of formula II is formed in situ.

The transition metal compound of formula VI can be prepared from commercial and readily available metal carbonyls, for example from trirutheniumdodecacarbonyl, with a tetradentate ligand of formula I, such as ligand L, by contacting the starting materials in an inert solvent.

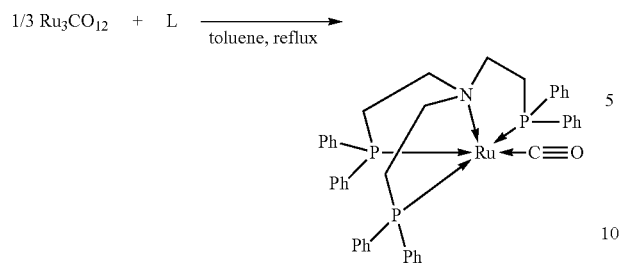

Suitable transition metal carbonyls can be $Mn_2CO_1$, $Re_2CO_1$, $FeCO_5$, $NiCO_4$, $Ru_3CO_{12}$, $Os_3CO_{12}$, $Co_2CO_8$, $Rh_4CO_{12}$ or $Ir_4CO_{12}$, preferably $Ru_3CO_{12}$ but also other precursors for the synthesis of the transition metal compound of formula VI can be used such as [Ru(PPh$_3$)$_3$(H)$_2$CO]. By contacting [Ru(PPh$_3$)$_3$(H)$_2$C] with a tetradentate ligand of formula I, such as ligand L, the three PPh$_3$ ligands are replaced and H$_2$ is released and the compound of formula VI is formed.

The present invention has following major advantages: The use of the transition metal catalyst TMC1 in the hydrogenation of carboxylic acid ester and in the formation of carboxylic acid esters from at least one primary alcohol does not require the addition of a base; the synthesis of the transition metal catalyst TMC1 can be realized in two steps from commercial starting materials; furthermore the same catalysts work for the ester hydrogenation as well as the dehydrogenative coupling of alcohols. Preferably an alcohol is chosen, which acts as an additive for catalyst activation, that is the formation of transition metal complexes of formula II, wherein said alcohol is identical with an alcohol formed by the ester hydrogenation or used as starting material in the dehydrogenative coupling reaction.

The invention is illustrated by the examples which follow, but these do not restrict the invention.

Figures in percent are each based on % by weight, unless explicitly stated otherwise.

General

All chemicals and solvents were purchased from Sigma-Aldrich or ABCR and used without further purification.

$^1$H-, $^{13}$C- and $^{31}$P NMR spectra were recorded on Bruker Avance 200 or 400 MHz spectrometer and were referenced to the residual proton ($^1$H) or carbon ($^{13}$C) resonance peaks of the solvent. Chemical shifts (δ) are reported in ppm. $^{31}$P NMR spectra were referred to an external standard (sample of $D_3PO_4$)

I. Preparation of Transition Metal Catalyst TMC1

I.1 Preparation of Tetradentate Ligands of Formula

I.1.a Preparation of tris(2-(diphenylphosphino)ethyl)amine (L)

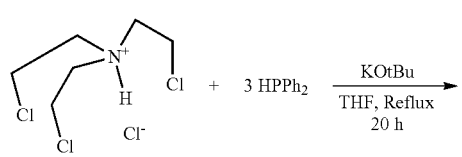

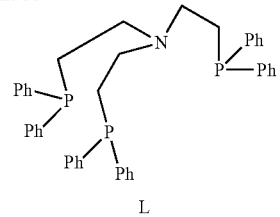

A 100 ml round bottom glass flask equipped with a condenser, was charged under argon with an anhydrous degassed solution of KOtBu (1.81 g) in THF (25 ml). Diphenylphosphine (1.1 mL, 6.3 mmol) was added under argon and the red/orange mixture was stirred for 5 minutes. 0.5 g tris(2-chloroethyl)ammoniumhydrochloride was added under argon and the mixture was heated to reflux for 20 h under argon. The mixture was then cooled to RT, and poured into degassed, deionized water (70 mL) in a round bottom glass flask. The flask was cooled in an ice bath for 1 h to induce precipitation. The precipitate was then filtered and rapidly washed with ethanol (2×10 mL). The white precipitate was dried under high vacuum to yield 1.1 g white powder (73% yield). The purity of the product was analyzed by $^1$H and $^{31}$P NMR spectroscopy and found to be >95% pure by 1H-NMR, and >99% pure by $^{31}$P{$^1$H}-NMR I.1.b Preparation of tris((2-(diphenylphosphino)ethyl)amino)ruthenium Monocarbonyl-Ru(L)CO (I)

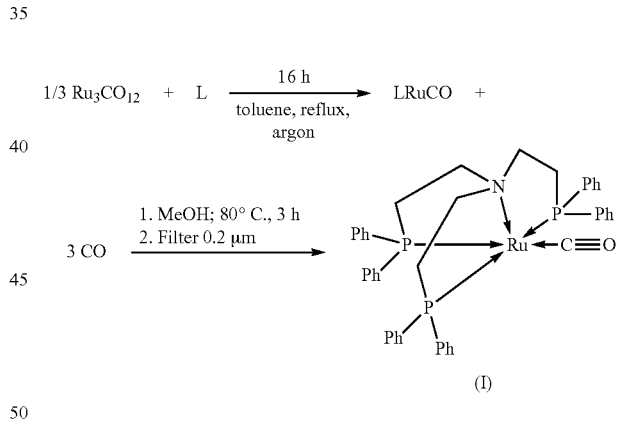

In a dry argon filled glove box, a 100 mL glass Schlenk flask was charged with triruthenium dodecacarbonyl (Ru$_3$CO$_{12}$, 162 mg) and tris(2-(diphenylphosphino)ethyl) amine (L, 500 mg) and toluene (15 ml). The flask was equipped with a condenser and the system was mounted under argon at a Schlenk line. The solution was heated in an oil bath to reflux (oil temperature 135° C.) with stirring under argon for 16 hrs. Upon cooling to room temperature, the product precipitated as an orange powder. The workup procedure was performed in an argon filled glove-box: The solvent was removed, and the orange powder was washed with degassed, dry benzene (20 ml). The orange residue was then introduced into a 100 ml Teflon capped pressure vessel, with degassed, dry benzene (25 ml). Degassed anhydrous methanol (2.5 ml) was added, and the solution was heated in the closed vessel, under argon, to 80° C. for 3 h, until a clear yellow solution was obtained. The solution was then cooled to room temperature and filtered through a 0.2 μm filter. The filtrate was evaporated fully under high vacuum to afford a bright orange powder (445 mg, 74% yield). The product was analyzed by elemental analysis (at the Mikroanalytisches Laboratorium der Chemischen Institute der Universität Heidelberg), and FTIR (Varian 2000, Scimitar Series, FTS2000).

I.1.c Preparation of methoxy [tris((2-(diphenylphosphino)ethyl)amino)hydridoruthenium monocarbonyl][RuH(L)CO]$^+$OMe$^-$

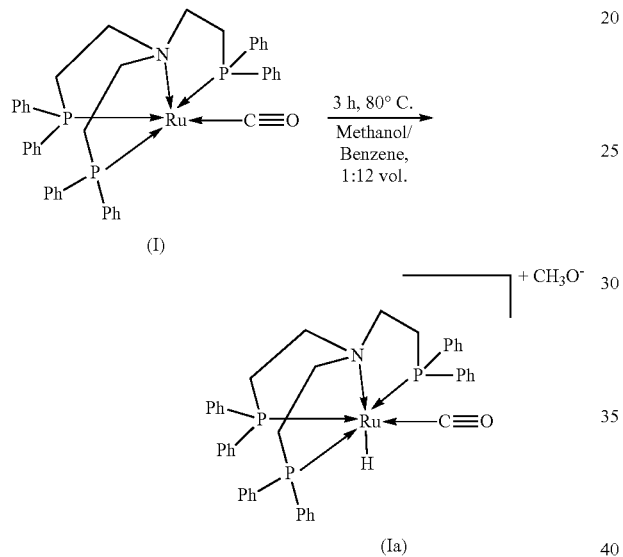

In a dry argon filled glove box, a 100 mL glass Schlenk flask was charged with Ru(L)CO (50 mg) and benzene (12 mL). Methanol (1.0 mL) was added and the flask was sealed with a Teflon cap. The solution was heated in an oil bath to 80° C. (oil temperature) with stirring under argon for 3 hours, by-which the orange slurry turned to a clear yellow solution. The product complex is only stable in solution, with excess methanol and was not isolated completely. The product was analyzed by NMR (Bruker 200, 400). Single crystals were grown by slow diffusion of diethyl ether/pentane to a benzene/methanol solution of the product. X-ray crystallography provided the confirmation of structure of the [RuH(L)CO]$^+$ cation.

$^1$H NMR (400 MHz, $C_6D_6$) δ 7.89 (dt, J=12.7, 4.1 Hz, 4H), 7.22 (dd, J=11.4, 4.2 Hz, 4H), 7.18-7.11 (m, 2H), 7.01-6.86 (m, 8H), 6.79 (t, J=7.4 Hz, 2H), 6.74-6.63 (m, 6H), 6.60 (td, J=7.6, 2.0 Hz, 4H), 3.16-2.96 (m, 4H), 2.73-2.60 (m, 4H), 2.50-2.32 (m, 4H), −6.60 (dt, J=83.0, 21.7 Hz, 1H).

$^{13}$C NMR (101 MHz, $C_6D_6$) δ 205.7 (td, J=12.0, 8.8 Hz), 160.0 (s), 138.3 (td, J=27.3, 4.6 Hz), 133.4 (t, J=6.4 Hz), 130.6-130.4 (m), 130.0 (t, J=5.6 Hz), 129.8 (d, J=11.3 Hz), 129.3 (s), 129.0 (d, J=1.9 Hz), 128.6 (t, J=4.7 Hz), 128.5 (d, J=4.6 Hz), 128.4-128.2 (m), 63.4 (t, J=4.4 Hz), 59.5 (d, J=7.8 Hz), 52.4 (s), 31.5 (d, J=23.6 Hz), 30.6 (t, J=13.4 Hz).

$^{31}$P NMR (81 MHz, $C_6D_6$) δ 55.7 (d, J=15 Hz), 44.6 (t, J=15 Hz).

I.1.d Preparation of Phenoxy [tris((2-(diphenylphosphino)ethyl)amino) hydridoruthenium monocarbonyl][RuH(L)CO]$^+$OPh$^-$

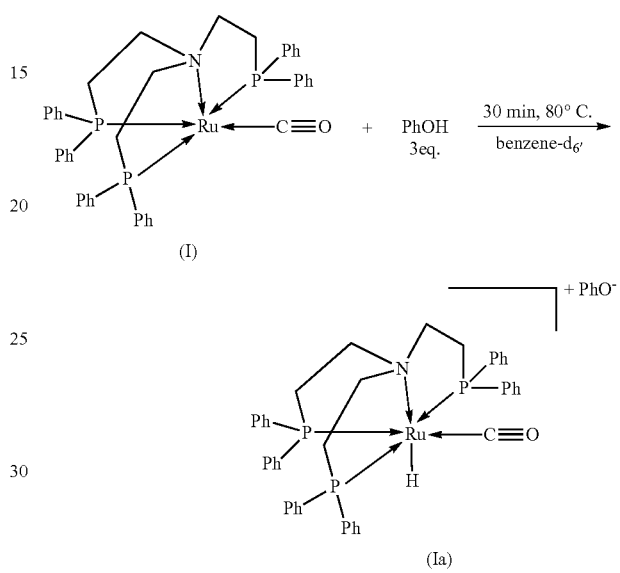

In a dry argon filled glove box, a capped NMR tube was charged with Ru(L)CO (22 mg) and benzene-$d_6$ (0.7 mL). Phenol (8 mg, 3 equiv) was added and the tube was shaken for 30 min. at 80° C. The solution turned to a clear yellow solution. The product was analyzed by NMR (Bruker 200, 400), and FTIR (Varian 2000, Scimitar Series, FTS2000).

$^1$H NMR (400 MHz, $C_6D_6$) δ 12.92 (b, 2H, free PhOH), 7.89 (dd, J=12.5, 6.5 Hz, 4H, PPh$_2$), 7.58 (dt, J=3.4, 1.7 Hz, 6H, PhO$^-$ and PhOH), 7.34-7.26 (m, 6H, PhO$^-$ and PhOH), 7.13 (dd, J=14.4, 7.1 Hz, 4H, PPh$_2$), 7.06-7.00 (m, 3H, PPh$_2$), 6.98 (ddd, J=9.8, 3.9, 1.5 Hz, 7H, PPh$_2$), 6.80-6.73 (m, 3H, PhO$^-$ and PhOH), 6.70-6.52 (m, 12H, PPh$_2$), 3.52 (dt, J=23.8, 6.7 Hz, 2H, NCH$_2$), 3.28 (dd, J=33.2, 17.2 Hz, 2H, NCH$_2$), 2.82 (dd, J=13.1, 6.5 Hz, 2H, NCH$_2$), 2.75-2.61 (m, 2H, CH$_2$P), 2.40-2.17 (m, 4H, 2(CH$_2$P)), −6.60 (dt, J=82.5, 21.4 Hz, 1H, Ru-H).

$^{13}$C NMR (101 MHz, $C_6D_6$) δ 206.7 (dt, J=20.7, 11.9 Hz), 139.3 (td, J=26.9, 4.7 Hz), 134.7 (dt, J=36.9, 2.1 Hz), 134.3 (td, J=20.8, 1.5 Hz), 134.0 (t, J=6.4 Hz), 130.6 (t, J=5.6 Hz), 130.6-130.5 (m, overlapping), 130.4 (m, overlapping), 129.3 (s), 129.0 (d, J=4.6 Hz), 128.8 (d, J=9.5 Hz), 128.6 (t, J=5.3 Hz), 63.9 (t, J=3.7 Hz), 60.3 (d, J=7.2 Hz), 32.3 (d, J=24.0 Hz), 31.2 (t, J=13.3 Hz).

$^{31}$P NMR (81 MHz, $C_6D_6$) δ 66.6 (d, J=15.0 Hz), 55.0 (t, J=15.0 Hz).

$v_{CO}$=1934 cm$^{-1}$

I.1.e Preparation of [tris((2-(diphenylphosphino)ethyl)amino) hydridoruthenium monocarbonyl]benzoate[RuH(L)CO]⁺PhCOO⁻

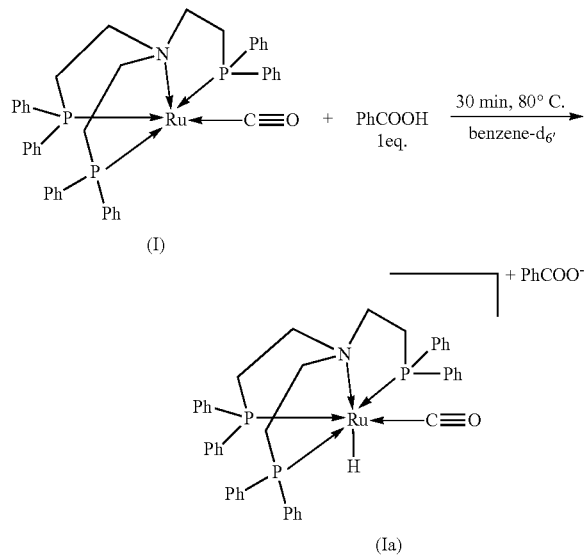

In a dry argon filled glove box, a capped NMR tube was charged with Ru(L)CO (15 mg) and benzene-d₆ (0.7 mL). Benzoic acid (2.3 mg, 1 equiv) was added and the tube was shaken for 30 min. at 80° C. The solution turned to a clear pale yellow solution. The product was analyzed by NMR (Bruker 200). Single crystals were grown by slow diffusion of diethyl ether to a benzene solution of the product. X-ray crystallography provided the confirmation of structure of the [RuH(L)CO]⁺PhCOO⁻ complex.

$^1$H NMR (200 MHz, C₆D₆) δ 9.18-8.86 (dd, J=8.2, 1.4 Hz, 2H, PhCOO), 7.96 (d, J=5.8 Hz, 4H, PPh₂), 7.53 (b, 1H, overlapping, PhCOO and PPh₂), 7.53-7.43 (m, 2H, overlapping, PhCOO), 7.33 (d, J=8.4 Hz, 8H, PPh₂), 7.14-6.91 (m, 8H, PPh₂), 6.67 (s, 10H, PPh₂), 4.78 (d, J=22.8 Hz, 2H, NCH₂—), 3.95 (m, N(CH₂-)₂), 2.74-2.15 (m, 4H, (—CH₂P)₂), −6.31 (dt, J=82.4, 20.4 Hz, 1H, Rh-H).

$^{31}$P NMR (81 MHz, C₆D₆) δ 68.4 (d, J=15.2 Hz), 57.6 (t, J=15.3 Hz).

II. Use of Transition Metal Catalysts TMC1 as Catalyst Hydrogenation of Esters and Formation of Esters by Dehydrogenative Coupling of Primary Alcohols

II.1 Base-Free Hydrogenation of Esters (Dimethyl Terephthalate) with MeOH as Activator

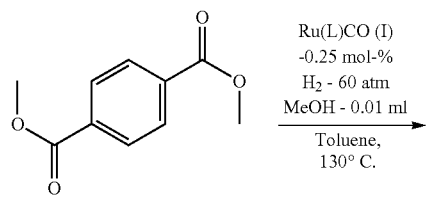

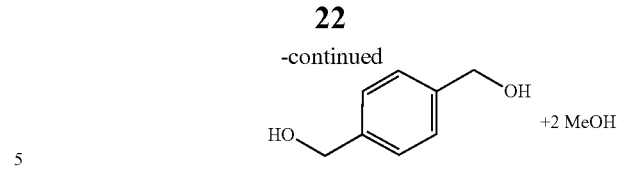
+2 MeOH

In a dry argon filled glove box, a 20 mL Teflon coated stainless steel autoclave was charged with the catalyst Ru(L)CO (I) (0.003 mmol), dimethyl terephthalate (1.2 mmol), methanol (0.01 mL) and toluene (6 mL). The argon atmosphere in the autoclave was replaced with H₂ by twice pressurization to 30 bar, and pressure release at room temperature. The autoclave was then pressurized with H₂ gas (60 bar). The solution was heated at 130° C. (heating mantel temperature) with stirring for 18 hrs. After cooling to 0° C., the system was vented carefully and purged for 1 minute with argon. The conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 mm/0.25 µm). Full conversion, with no residual dimethyl terephthalate was observed. The solution was then filtered, and the product 1,4-phenylenedimethanol, was collected and dried under vacuum. 147 mg product (90% yield) were obtained as a white crystalline powder. The product identification and purity (>99%) were analyzed by $^1$H-NMR (tetrachloroethane as internal standard, 200 MHz Bruker Avance, in CD₃O).

II.2 Base-Free Hydrogenation of Esters (Dimethyl Terephthalate) without an Alcohol as Activator (Comparative Example)

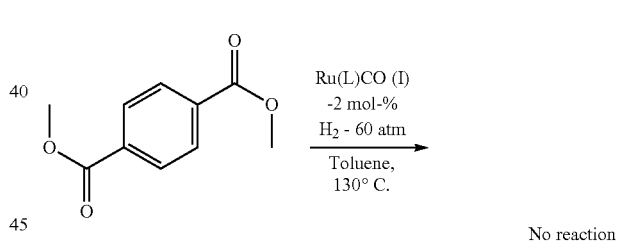

No reaction

In a dry argon filled glove box, a stainless steel autoclave was charged with the catalyst Ru(L)CO (I) (0.02 mmol), dimethyl terephthalate (1 mmol), and toluene (14 mL). The argon atmosphere in the autoclave was replaced with H₂ by twice pressurization to 30 bar, and pressure release at room temperature. The autoclave was then pressurized with H₂ gas (60 bar). The solution was heated at 130° C. (heating mantel temperature) with stirring for 18 hrs. After cooling to 0° C., the system was vented carefully and purged for 1 minute with argon. The conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 mm/0.25 µm). No conversion was detected, dimethyl terephthalate as the only component was observed.

II.3 Base-Free Hydrogenation of Esters (Ethylacetate) with EtOH as Activator

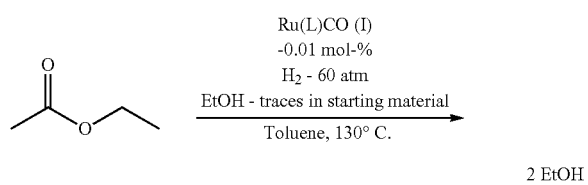

In a dry argon filled glove box, a 20 mL Teflon lined stainless steel autoclave was charged with the catalyst Ru(L)CO (I) (0.008 mmol), and ethyl acetate (5.0 mL, 85.7 mmol, anhydrous, 99.8% purchased from Sigma Aldrich). The ethylacetate used contained 0.01% EtOH (determined by GC; amount given in GC area %) which is a sufficient amount to act as catalyst activator. The argon atmosphere in the autoclave was replaced with $H_2$ by twice pressurization to 30 bar, and pressure release at room temperature. The autoclave was then pressurized with $H_2$ gas (60 bar). The solution was heated at 130° C. (heating mantel temperature) with stirring for 40 hrs. After cooling to 0° C., the system was vented carefully and purged for 1 minute with argon. The product solution was analyzed by $^1$H-NMR (tetrachloroethane as internal standard, 200 MHz Bruker Avance, in $C_6D_6$). Yield measured to be 91%, corresponding to a turn over number (TON) of 5700.

II.4 Base-Free Dehydrogenative Coupling of Alcohols (1-Pentanol) to Esters (Pentyl Pentanoate)

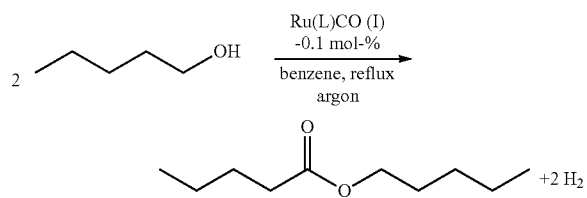

In a dry argon filled glove box, a 100 mL round-bottomed glass Schlenk flask was charged with the catalyst Ru(L)CO (I) (0.006 mmol), 1-pentanol (0.48 mL, 4.41 mmol), and benzene (10 mL). The flask was equipped with a condenser and the system was mounted under argon at a Schlenk line. The solution was heated in an oil bath to reflux (oil temperature 100° C.) with stirring under argon for 18 hrs. After cooling to room temperature the conversion of starting material was analyzed by GC on an Agilent Technologies 6890N gas chromatography system equipped with a FID detector and an Agilent Technologies DB-1 capillary column (30 m×0.250 mm/1.0 μm). Full conversion was observed. The solution was then eluted through a silica column in pentanes/ethyl acetate (9:1) and the combined fractions to yield 296 mg as a colorless liquid. The product identification and purity were analyzed by $^1$H-NMR (tetrachloroethane as internal standard, 200 MHz Bruker Avance, in $C_6D_6$). Isolated yield measured to be 78%.

II.5 Base-Free Dehydrogenative Coupling of Alcohols (1-hexanol) to Esters (Hexyl Hexanoate)

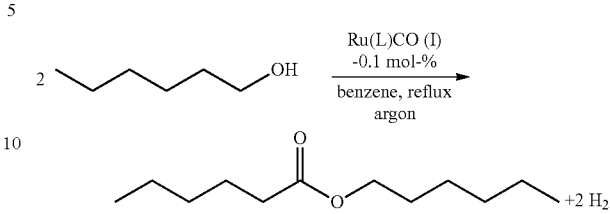

In a dry argon filled glove box, a 100 mL round-bottomed glass Schlenk flask was charged with the catalyst Ru(L)CO (I) (0.01 mmol), 1-hexanol (13.5 mmol), and toluene (10 mL). The flask was equipped with a condenser and the system was mounted under argon at a Schlenk line. The solution was heated in an oil bath to reflux (oil temperature 135° C.) with stirring under argon for 18 hrs. After cooling to room temperature the conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 mm/0.25 μm). 97% conversion (by area) was measured. The solution was then evaporated under vacuum, and the product hexyl hexanoate, was collected and dried under vacuum. 1.26 g product (93% yield) were obtained as a colorless liquid. The product identification and purity were analyzed by $^1$H-NMR (tetrachloroethane as internal standard, 200 MHz Bruker Avance, in $C_6D_6$). Isolated yield measured to be 90%.

II.6 Rehydrogenation of Hexyl Hexanoate, Formed by Additive-Free Dehydrogenation of Hexanol

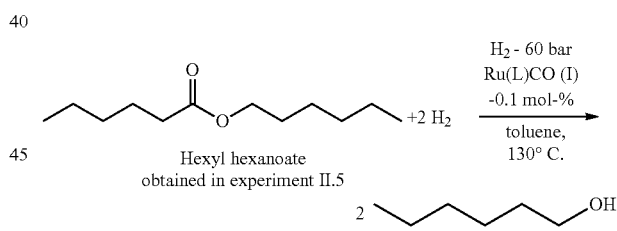

In a dry argon filled glove box, the product from the above (Example 5) described dehydrogenative coupling of hexanol to hexyl hexanoate: 1.2 g hexyl hexanoate, at 97% purity, containing catalyst carried over from dehydrogenation, with 0.5 mol % hexanol (determined by GC-FID; amount given in GC-area %), along with toluene (5 mL) were charged in a 20 mL Teflon lined stainless steel autoclave. The argon atmosphere in the autoclave was replaced with $H_2$ by twice pressurization to 30 bar, and pressure release at room temperature. The autoclave was then pressurized with $H_2$ gas (60 bar). The solution was heated at 130° C. (heating mantel temperature) with stirring for 18 hrs. After cooling to 0° C., the system was vented carefully and purged for 1 minute with argon. The conversion of starting material was analyzed by GC on an Agilent Technologies 6890N gas chromatography system equipped with a FID detector and an Agilent Technologies DB-1 capillary column (30 m×0.250 mm/1.0 μm). The solution was then fully evaporated, yielding 1.1 g product as a slightly pale yellow liquid. Purity was measured by $^1$H-NMR (tetrachloroethane as internal standard, 200 MHz Bruker Avance, in $C_6D_6$). Yield measured to be 88%.

II.7 Hydrogenation of Symmetric Esters, or Methyl Esters Catalyzed by Ru(L)CO Activated by Methanol. General Procedure

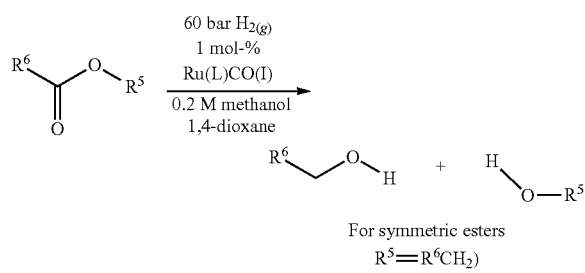

For symmetric esters
$R^5 = R^6CH_2$

In an argon filled glove-box, a ca. 80 mL Premex stainless steel autocalve fitted with a PTFE inner chamber and a PTFE coated magnetic stirring bar was charged with Ru(L)CO (I) ($6\times10^{-3}$ mmol, 4.7 mg), the specified ester (0.6 mmol), degassed, anhydrous 1,4-dioxane (6.0 mL) and degassed anhydrous methanol (0.05 mL). Hexamethylbenzene (0.15 mmol, as internal standard) was added and the mixture was stirred vigorously at room temperature until full dissolution. A sample (0.1 mL) was then taken for $t_0$-analysis (GC and NMR). After closing the reaction vessel was removed from the glove-box. The argon atmosphere in the autoclave was replaced with $H_2$ by twice pressurization to 30 bar, and pressure release at room temperature. The autoclave was then pressurized with $H_2$ gas (60 bar). The solution was heated at 130° C. (heating mantel temperature) with stirring for 17 hrs. After cooling to 0° C., the system was vented carefully and purged for 1 minute with argon. A sample of the crude mixture (0.1 mL) was transferred to a vial and was analyzed as-is by GC on an Agilent Technologies 6890N gas chromatography system equipped with a FID detector and an Agilent Technologies DB-1 capillary column (30 m×0.250 mm/1.0 μm). Another sample (0.1 mL) was diluted with $CDCl_3$ (0.6 mL) in an NMR tube and analyzed by $^1$H-NMR. Conversion was determined by comparison to the samples at to (with hexamethylbenzene as internal standard). NMR yield was determined by the ratio of product to starting material in the crude sample after reaction.

TABLE 1

| Entry | ester | alcohol | Conv. (Yield)[b] |
|---|---|---|---|
| II.7.1 | methyl 4-(trifluoromethyl)benzoate | 4-(trifluoromethyl)benzyl alcohol | >99 |
| II.7.2 | methyl 4-methoxybenzoate | 4-methoxybenzyl alcohol | >99 |
| II.7.3 | methyl picolinate | 2-pyridinylmethanol | >99 |
| II.7.4 | lactide | propylene glycol | >99 |

TABLE 1-continued

| Entry | ester | alcohol | Conv. (Yield)[b] |
|---|---|---|---|
| II.7.5 | (dimethyl terephthalate structure) | (4-(hydroxymethyl)benzyl alcohol structure) | 80 |
| II.7.6 | | | >99 (>99)[d] |

[a]Reaction conditions: ester (0.1 M), Ru(L)CO (I) (1 mol %), and 1,4-dioxane (6 mL) were pressurized with 60 bar $H_2$ and heated at 130° C. (heating block temperature) for 17 h.
[b]Percent conversion, in solution, by % area in GC-FID, and confirmed by $^1$H-NMR in $CDCl_3$ with hexamethylbenzene as internal standard.
[c]Performed in toluene.
[d]Percent yield determined after isolation of 2f by partial evaporation and filtration, by $^1$H-NMR in $CD_3OD$ with 1,1,2,2-tetrachloroethane as internal standard

II.8 Base-Free Hydrogenation of Esters (Dimethyl Terephthalate) with Phenol as Activator

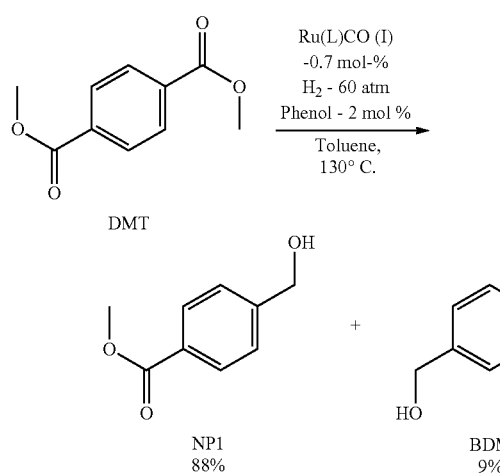

II.9 Hydrogenation of Esters (Dimethyl Terephthalate) Catalyzed by [Ru(L)CO(H)]⁺PhCOO⁻ with Methanol as Activator

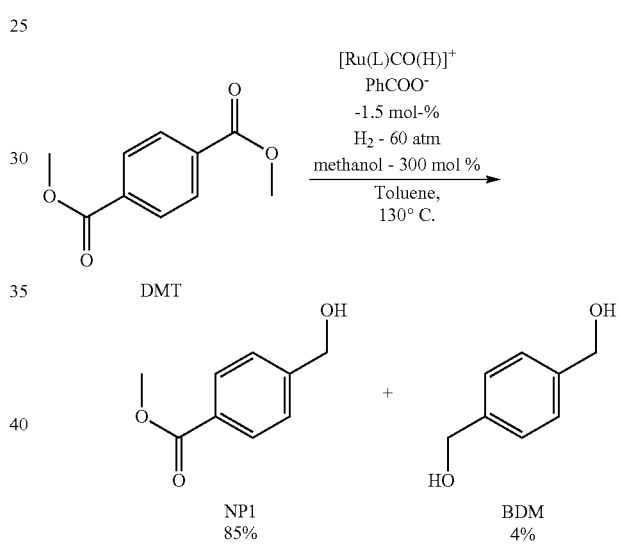

In a dry argon filled glove box, a stainless steel autoclave was charged with the catalyst Ru(L)CO (I) (0.02 mmol), and phenol (0.04 mmol) and toluene (12 mL). The mixture was stirred for 30 min at RT. Then dimethyl terephthalate (3 mmol) was added. The argon atmosphere in the autoclave was replaced with $H_2$ by twice pressurization to 30 bar, and pressure release at room temperature. The autoclave was then pressurized with $H_2$ gas (60 bar). The solution was heated at 130° C. (heating mantel temperature) with stirring for 18 hrs. After cooling to 0° C., the system was vented carefully and purged for 1 minute with argon. The conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 mm/0.25 μm). The solution was then evaporated under vacuum to remove all volatiles, and a sample was measured by $^1$H-NMR in methanol-$d_4$ with 1,1,2,2-tetrachloroethane as internal standard. 88% yield of NP1 was obtained with a ratio of: 10/1/0.4 of the components NP1:BDM:DMT respectively.

In a dry argon filled glove box, a ca. 80 mL Premex stainless steel autocalve fitted with a PTFE inner chamber and a PTFE coated magnetic stirring bar was charged with the complex [Ru(L)CO(H)]⁺PhCOO⁻ (0.015 mmol), dimethyl terephthalate (1.0 mmol) and toluene (6 mL). Methanol was added (0.1 mL) and the autoclave was sealed. The argon atmosphere in the autoclave was replaced with $H_2$ by twice pressurization to 30 bar, and pressure release at room temperature. The autoclave was then pressurized with $H_2$ gas (60 bar). The solution was heated at 130° C. (heating mantel temperature) with stirring for 19 hrs. After cooling to 0° C., the system was vented carefully and purged for 1 minute with argon. The conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 mm/0.25 μm). By % area, ca. 85% NP1 was obtained, with LT 5% BDM, and then rest unreacted DMT.

II.10 Base-Free Hydrogenation of Esters (Dimethyl terephthalate) with Ru(PPh₃)(CO)₂ (PPh₃=tris-(diphenylphosphinoethyl)phosphine)—Comparative Example

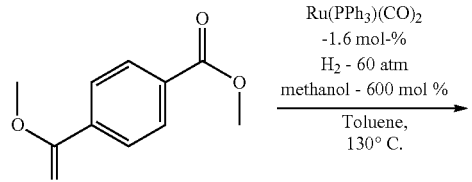

No reaction

In a dry argon filled glove box, a stainless steel autoclave was charged with the complex Ru(PPh₃)(CO)₂ (0.008 mmol), dimethyl terephthalate (0.5 mmol), and toluene (6 mL). Methanol was added (0.1 mL) and the autoclave was sealed. The argon atmosphere in the autoclave was replaced with H₂ by twice pressurization to 30 bar, and pressure release at room temperature. The autoclave was then pressurized with H₂ gas (60 bar). The solution was heated at 130° C. (heating mantel temperature) with stirring for 19 hrs. After cooling to 0° C., the system was vented carefully and purged for 1 minute with argon. The conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 mm/0.25 μm). No conversion was detected, dimethyl terephthalate as the only component was observed.

II.11 Base-Free Hydrogenation of Esters (Dimethyl terephthalate) with Ru₃(CO)₁₂+ Triphos (Triphos=1,1,1-Tris(diphenylphosphinomethyl)ethane)—Comparative Example

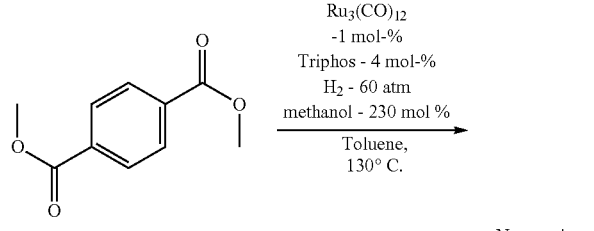

No reaction

In a dry argon filled glove box, a stainless steel autoclave was charged with the complex Ru₃(CO)₁₂ (0.01 mmol), Triphos (0.04 mmol), dimethyl terephthalate (1.08 mmol), and toluene (6 mL). Methanol was added (0.1 mL) and the autoclave was sealed. The argon atmosphere in the autoclave was replaced with H₂ by twice pressurization to 30 bar, and pressure release at room temperature. The autoclave was then pressurized with H₂ gas (60 bar). The solution was heated at 130° C. (heating mantel temperature) with stirring for 17 hrs. After cooling to 0° C. the system was vented carefully and purged for 1 minute with argon. The conversion of starting material was analyzed by GC-MS, using an Agilent Technologies 6890N gas chromatography system coupled with an Agilent Technologies 5975B mass spectrometer and equipped with an Agilent Technologies HP-5MS capillary column (30 m×0.250 m/0.25 μm). No conversion was detected, only starting material was observed.

II.12 Hydrogenation of Unsaturated Esters (methyl trans-3-hexenoate) Catalyzed by Ru(L)CO with Methanol as Activator

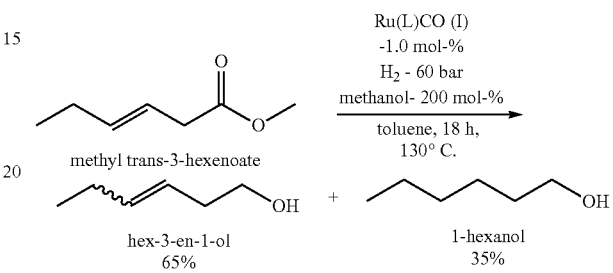

In a dry argon filled glove box, a ca. 80 mL Premex stainless steel autocalve fitted with a PTFE inner chamber and a PTFE coated magnetic stirring bar was charged with the complex Ru(L)CO (0.006 mmol), methyl trans-3-hexenoate (0.6 mmol) and toluene (6 mL). Methanol was added (0.05 mL) and the autoclave was sealed. The argon atmosphere in the autoclave was replaced with H₂ by twice pressurization to 30 bar, and pressure release at room temperature. The autoclave was then pressurized with H₂ gas (60 bar). The solution was heated at 130° C. (heating mantel temperature) with stirring for 18 hrs. After cooling to 0° C., the system was vented carefully and purged for 1 minute with argon. The conversion of starting material was analyzed by GC on an Agilent Technologies 6890N gas chromatography system equipped with a FID detector and an Agilent Technologies DB-1 capillary column (30 m×0.250 mm/1.0 μm). Another sample (0.1 mL) was diluted with CDCl₃ (0.6 mL) in an NMR tube and analyzed by ¹H-NMR. Full conversion of the starting material was measured, to a mixture of ca. 65% hex-3-en-1-ol, and ca. 35% 1-hexnaol (as well as methanol).

II.13 Hydrogenation of Sclareolide (3a,6,6,9a-tetramethyl-1,4,5,5a,7,8,9,9b-octahydronaphtho[8,7-d]furan-2-one)

Ru₃(CO)₁₂ (8.5 mg, 0,013 mmol), tris(2-(diphenylphosphinol)ethyl)amine (L) (26 mg, 0.04 mmol), NaOMe (27 mg, 0.5 mmol) and (3aR)-(+)-Sclareolide (Sigma-Aldrich, 2.5 g, 10 mmol) are transferred into a stainless steel autoclave (V2A steel, Premex) under inert atmosphere. THF (40 mL, dry) was added finally into the autoclave. The autoclave was then pressurized with H₂ gas (60 bar) and stirred at 700 rpm. The solution was heated to 150° C. (solution temperature) for 16 hrs and the pressure was kept at 80 bar. The conversion of starting material was analyzed by GC, using an Optima FFAP column (30 m×0.25 mm/0.5 μm; 15 min at 140° C. then heat with 20° C./min to 250° C.; const. flow: 2.0 ml/min; Helium as carrier gas). Conversion (GC-area %) was 75% and the selectivity for Ambroxdiol was 90%. $t_R$(Sclareolide)=29.4 min; $t_R$(Ambroxdiol)=32.5 min.

II.14 Hydrogenation of Sclareolide (3a,6,6,9a-tetramethyl-1,4,5,5a,7,8,9,9b-octahydronaphtho[8,7-d]furan-2-one) (Base-Free Conditions)

Ru$_3$(CO)$_{12}$ (8.5 mg, 0,013 mmol), tris(2-(diphenylphosphinol)ethyl)amine (26 mg, 0.04 mmol) and (3aR)-(+)-Sclareolide (Sigma-Aldrich, 2.5 g, 10 mmol) are transferred into a stainless steel autoclave (V2A steel, Premex) under inert atmosphere. THF (40 mL, dry) was added finally into the autoclave. The autoclave was then pressurized with H$_2$ gas (60 bar) and stirred at 700 rpm. The solution was heated to 150° C. (solution temperature) for 16 hrs and the pressure was kept at 80 bar. The conversion of starting material was analyzed by GC, using an Optima FFAP column (30 m×0.25 mm/0.5 µm; 15 min at 140° C. then heat with 20° C./min to 250° C.; const. flow: 2.0 ml/min; Helium as carrier gas). Conversion (GC-area %) was 90% and the selectivity for Ambroxdiol was 89%. t$_R$(Sclareolide)=29.4 min; t$_R$(Ambroxdiol)=32.5 min.

The invention claimed is:

1. A transition metal catalyst TMC1 comprising:
ruthenium,
a tetradentate ligand of formula I,

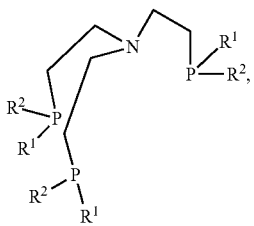

wherein R$^1$ are each independently selected from the group consisting of a C$_1$ to C$_{40}$ alkyl radical, a C$_3$ to C$_{40}$ cycloalkyl radical, a C$_2$ to C$_{40}$ heterocycloalkyl radical, a C$_6$ to C$_{40}$ aryl radical, and a C$_2$ to C$_{40}$ heteroaromatic radical, and
wherein R$^2$ are each independently selected from the group consisting of a C$_1$ to C$_{40}$ alkyl radical, a C$_3$ to C$_{40}$ cycloalkyl radical, a C$_2$ to C$_{40}$ heterocycloalkyl radical, a C$_6$ to C$_{40}$ aryl radical, and a C$_2$ to C$_{40}$ heteroaromatic radical, and
a carbon monoxide ligand and comprising one or more additional ligands selected from the group consisting of hydrides, alkoxides, aryloxides, carboxylates and acyls.

2. The transition metal catalyst of claim 1, wherein R$^1$ and R$^2$ are identical.

3. The transition metal catalyst of claim 1, further comprising one or more additional ligands, comprising a neutral ligand selected from the group consisting of triaryl phosphines, amines, N-heterocyclic carbenes and isonitriles.

4. The transition metal catalyst of claim 1, wherein R$^1$ are each identical and wherein R$^2$ are each identical.

5. The transition metal catalyst of claim 1, wherein R$^1$ and R$^2$ are each independently an alkyl radical selected from the group consisting of methyl, ethyl, 1-propyl, 2-propyl, 1-butyl, 1-hexyl, 1-octyl-iso-butyl, adamantyl, 2-pyridyl, 3-pyridyl, 4-pyridyl, cyclohexyl, cyclopentyl, tert.-butyl, p-tert.-butyl-phenyl, o-tolyl, m-tolyl, p-tolyl, p-methoxyphenyl, p-trifluoromethyl-phenyl, 4-biphenyl, naphthyl and phenyl.

6. A transition metal complex of formula II:

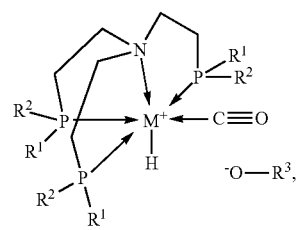

wherein M is ruthenium,
wherein R$^1$ are each independently selected from the group consisting of a C$_1$ to C$_{40}$ alkyl radical, a C$_3$ to C$_{40}$ cycloalkyl radical, a C$_2$ to C$_{40}$ heterocycloalkyl radical, a C$_6$ to C$_{40}$ aryl radical, and a C$_2$ to C$_{40}$ heteroaromatic radical, and
wherein R$^2$ are each independently selected from the group consisting of a C$_1$ to C$_{40}$ alkyl radical, a C$_3$ to C$_{40}$ cycloalkyl radical, a C$_2$ to C$_{40}$ heterocycloalkyl radical, a C$_6$ to C$_{40}$ aryl radical, and a C$_2$ to C$_{40}$ heteroaromatic radical, and
wherein R$^3$ is selected from the group consisting of a C$_1$ to C$_{40}$ alkyl radical, a C$_3$ to C$_{40}$ cycloalkyl radical, a C$_2$ to C$_{40}$ heterocycloalkyl radical, a C$_6$ to C$_{40}$ aryl radical, a C$_7$ to C$_{40}$ arylalkyl radical, and a C$_2$ to C$_{40}$ heteroaromatic radical, or
wherein R$^3$ is C(=O)R$^4$, wherein R$^4$ is selected from the group consisting of a hydrogen, a C$_1$ to C$_{40}$ alkyl radical, a C$_3$ to C$_{40}$ cycloalkyl radical, a C$_2$ to C$_{40}$ heterocycloalkyl radical, a C$_6$ to C$_{40}$ aryl radical, a C$_7$ to C$_{40}$ arylalkyl radical, and a C$_2$ to C$_{40}$ heteroaromatic radical, wherein R$^3$ in each case is bound via a carbon atom to the oxygen atom.

7. The transition metal complex of claim 6, wherein R$^1$ are each identical and wherein R$^2$ are each identical.

8. The transition metal complex of claim 6, wherein R$^1$ and R$^2$ are identical.

9. The transition metal complex of claim 6, wherein R$^1$ and R$^2$ are each independently an alkyl radical selected from the group consisting of methyl, ethyl, 1-propyl, 2-propyl, 1-butyl, 1-hexyl, 1-octyl-iso-butyl, adamantyl, 2-pyridyl, 3-pyridyl, 4-pyridyl, cyclohexyl, cyclopentyl, tert.-butyl, p-tert.-butyl-phenyl, o-tolyl, m-tolyl, p-tolyl, p-methoxyphenyl, p-trifluoromethyl-phenyl, 4-biphenyl, naphthyl and phenyl.

10. The transition metal complex of claim 6, wherein R$^3$ is a C$_1$ to C$_6$ alkyl radical comprising methyl, ethyl, isopropyl, cyclohexyl, cyclopentyl or tert.-butyl, or a substituted or unsubstituted C$_6$ to C$_{18}$ aryl radical comprising p-tert.-butyl-phenyl, o-tolyl, m-tolyl, p-toly, naphthyl or phenyl, or a substituted or unsubstituted C$_7$ to C$_{18}$ arylalkyl radical comprising benzyl.

11. The transition metal complex of claim 6, wherein R$^3$ is a C$_1$ to C$_{15}$ alkanoyl radical comprising formyl, acetyl or propionyl, or a substituted or unsubstituted benzoyl.

12. A transition metal catalyst comprising:
a transition metal complex of formula II:

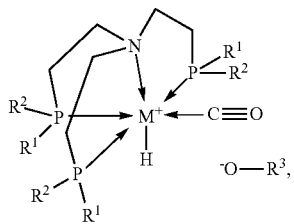

wherein M is ruthenium,
wherein $R^1$ are each independently selected from the group consisting of a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical, and a $C_2$ to $C_{40}$ heteroaromatic radical, and
wherein $R^2$ are each independently selected from the group consisting of a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical, and a $C_2$ to $C_{40}$ heteroaromatic radical, and
wherein $R^3$ is selected from the group consisting of a $C_1$ to $C_{40}$ alkyl radical, a $C_3$ to $C_{40}$ cycloalkyl radical, a $C_2$ to $C_{40}$ heterocy-cloalkyl radical, a $C_6$ to $C_{40}$ aryl radical, a $C_7$ to $C_{40}$ arylalkyl radical, and a $C_2$ to $C_{40}$ heteroaromatic radical, or
wherein $R^3$ is C(=O)$R^4$, wherein $R^4$ is selected from the group consisting of a hydrogen, a $C_1$ to $C_{40}$ alkyl radical, a $C_3$ to $C_{40}$ cycloalkyl radical, a $C_2$ to $C_{40}$ heterocycloalkyl radical, a $C_6$ to $C_{40}$ aryl radical, a $C_7$ to $C_{40}$ arylalkyl radical, and a $C_2$ to $C_{40}$ heteroaromatic radical, wherein $R^3$ in each case is bound via a carbon atom to the oxygen atom; and
one or more ligand comprising an anion selected from the group consisting of hydrides, alkoxides, aryloxides, carboxylates and acyls, or a neutral ligand selected from the group consisting of carbon monoxide, triaryl phosphines, amines, N-heterocyclic carbenes and isonitriles.

13. A composition comprising:
the transition metal catalyst of claim 1; and
a liquid reaction mixture,
wherein the transition metal catalyst is in an amount of about 0.1 ppm to about 2000 ppm (parts per weight) based on the total weight of the liquid reaction mixture.

14. A composition comprising:
the transition metal complex of claim 6; and
a liquid reaction mixture,
wherein the transition metal complex is present in an amount of about 0.1 ppm to about 2000 ppm (parts per weight) based on the total weight of the liquid reaction mixture.

15. A method of using the transition metal catalyst of claim 1 for base-free hydrogenation of dimethyl terephthalate, comprising:
contacting the dimethyl terephthalate with the transition metal catalyst in the presence of hydrogen without adding a base,
wherein the transition metal catalyst provides about a 90% yield of 1,4-phenylenedimethanol.

* * * * *